United States Patent [19]

Heckles

[11] 4,046,803

[45] Sept. 6, 1977

[54] METHOD OF PREPARING β-AMINO DERIVATIVES OF α,β-UNSATURATED ESTERS

[75] Inventor: John S. Heckles, Lancaster, Pa.

[73] Assignee: Armstrong Cork Company, Lancaster, Pa.

[21] Appl. No.: 736,107

[22] Filed: Oct. 27, 1976

[51] Int. Cl.$^2$ .......................................... C07C 119/12
[52] U.S. Cl. .................................................. 560/172
[58] Field of Search ................................... 260/482 R

[56] References Cited

U.S. PATENT DOCUMENTS

| 2,822,377 | 2/1958 | Kaiser | 260/482 R |
|---|---|---|---|
| 2,852,527 | 9/1958 | Steck | 260/482 R |
| 2,987,491 | 6/1961 | Bader | 260/482 R |
| 3,137,698 | 6/1964 | Pfister | 260/482 R |
| 3,235,361 | 2/1966 | Loux | 260/482 R |
| 3,412,139 | 11/1968 | Eggensperger | 260/482 R |

FOREIGN PATENT DOCUMENTS

| 59,086 | 1970 | Germany | 260/482 R |
|---|---|---|---|
| 804,442 | 1951 | Germany | 260/482 R |
| 47-18825 | 1972 | Japan | 260/482 R |
| 47-18827 | 1972 | Japan | 260/482 R |

*Primary Examiner*—Lorraine A. Weinberger
*Assistant Examiner*—Michael Shippen
*Attorney, Agent, or Firm*—Richard J. Hammond

[57] ABSTRACT

A method for the preparation of β-amino derivatives of α,β-unsaturated esters of the formula $CH_3C(NH_2)=CHCOOR'$ where R' is $C_1$ to $C_{10}$ linear or branched alkyl or substituted $C_1$ to $C_{10}$ linear or branched alkyl. A reaction mixture of an acetoacetate ester of the formula $CH_3C(O)CH_2C(O)OR'$ wherein R' is the same as defined above is first formed in an organic solvent and this mixture reacted with aqueous ammonium hydroxide in the presence of a salt of ammonia or of a metal selected from the group consisting of lithium, zinc, cadmium, cerium and lead. The salt is soluble in the organic solvent to an extent sufficient to catalyze the reaction between ammonia and the ester.

7 Claims, No Drawings

METHOD OF PREPARING β-AMINO DERIVATIVES OF α,β-UNSATURATED ESTERS

This invention relates to the method for preparing amine esters. More particularly, it relates to a method for preparing β-amino derivatives of α,β-unsaturated esters.

Alkyl β-amino crotonate and alkyl β-alkylamino crotonate esters are well-known in the prior art. See, for example, Vonauwers and Susemihl, Berichte, Volume 63, 1072 (1930). These materials have significant utility as intermediates in the preparation and purification of various metals and metal ion solutions because of their ability to act as metal complexing agents, e.g., chelating agents.

When alkyl acetoactates and any metals comprising copper, iron, magnesium or nickel salts are reacted in solution with aqueous ammonium hydroxide, a metal acetoacetate complex is obtained. Surprisingly, this does not occur when salts of ammonia or of metals comprising lithium, zinc, cadmium, cerium and lead are employed in accordance with the present invention.

A novel method for preparing β-amino α,β-unsaturated esters has now been developed wherein an alkyl acetoacetic ester of the formula $CH_3C(O)CH_2C(O)OR'$ wherein R' is $C_1$ to $C_{10}$ linear or branched alkyl or substituted $C_1$ to $C_{10}$ linear or branched alkyl is reacted with aqueous ammonium hydroxide in a solvent containing a catalyst. The catalysts are salts of ammonia or salts of metals selected from the group consisting of lithium, zinc, cadmium, cerium and lead, or mixtures thereof, the salts being soluble in the organic solvent to an extent sufficient to catalyze the reaction between the ester and ammonia. The reaction product is readily recovered simply by extracting the solution with a solvent that dissolves the β-amino α,β-unsaturated ester.

The following equations are illustrative of the series of reactions in which ethyl acetoacetate is used as a starting material for the catalytic preparation of β-amino α,β-unsaturated esters in accordance with the present invention:

$$(CH_2\!\!=\!\!C\!\!=\!\!O)_2 + C_2CH_3CH_2OH \xrightarrow{H\pm} CH_3COCHCOOC_2H_5 \quad (1)$$

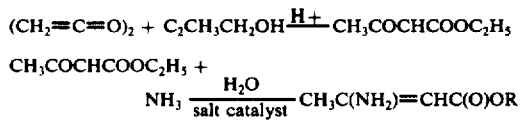

Heretofore, β-amino derivatives of α,β-unsaturated esters have been prepared by rapidly passing in a stream of dry ammonia gas through a lower alkyl acetoacetate solution at elevated temperatures. In these prior art processes, the yields for the lower alkyl esters, e.g., $C_1$ to $C_4$ are good. However, as alkyl branching or chain length increases, yields decrease significantly. Further, high reaction temperatures and long reaction times are necessary to even approach yields that are of economic utility. An advantage to the catalytic method in accordance with the present invention is that improved yields of the β-amino α,β-unsaturated materials are obtained at lower temperatures and shorter reaction times.

The solvent employed for a reaction of the starting materials can be any organic solvent that dissolves the ammonium salt or metal salt catalyst sufficiently so as to promote the desired reactions. Such solvent need not be anhydrous. Thus, common, low-boiling solvents such as the aromatic solvents, e.g., benzene, toluene, etc.; aliphatic alcohol solvents, e.g., methanol, ethanol, etc.; and the Freon solvents can be used in this invention. The solvent of preference herein is ethanol, methanol, or mixtures thereof.

The method of this invention provides an improvement in the type of reaction in which an amino group is substituted for the oxygen on the beta carbon of an acetoacetic acid ester to form a β-amino ester of the formula $CH_3C(NH_2)\!\!=\!\!CHC(O)OR'$ wherein R' is $C_1$ to $C_{10}$ linear or branched alkyl or substituted $C_1$ to $C_{10}$ linear or branched alkyl. The method applies in general to any such alkyl ester. The alkyl acetoacetates used in the process can be represented by the formula $CH_3C(O)CH_2C(O)OR'$, wherein R' is $C_1$ to $C_{10}$ linear or branched alkyl or substituted $C_1$ to $C_{10}$ linear or branched alkyl as defined above. When substituents are present, such should be those that would not interfere with the amination reaction and can include such radicals as $C_1$ to $C_{10}$ alkyl, $C_1$ to $C_{10}$ alkoxy, $C_6$ to $C_{10}$ aryl, $C_1$ to $C_4$ alkyl substituted aryl, $C_1$ to $C_4$ alkoxy substituted aryl, $C_5$ to $C_{10}$ heterocyclic, and the like. $C_1$ to $C_8$ linear or branched alkyl and $C_1$ to $C_4$ alkoxy substituted $C_1$ to $C_8$ linear or branched alkyl are preferred. Illustrative of such are methyl, ethyl, ethoxyethyl, butoxyethyl, propyl, butyl, pentyl, butoxyhexyl, hexyl, heptyl, octyl, 2-ethylhexyl, decyl, isodecyl, and the like.

As a second reactant with the alkyl acetoacetic ester is an aqueous solution of ammonia gas, sometimes referred to herein as aqueous ammonium hydroxide or concentrated ammonium hydroxide. Such is readily available in the form of ammonia gas-saturated aqueous solutions of specific gravity 0.881g/cc and about 35% ammonia.

As indicated in the reaction equations, an ammonium salt, a metal salt or mixtures thereof is used as a catalyst in the aforementioned reaction to cause enhanced yields, lower reaction temperatures, and shorter reaction times for the β-amino derivatives of α,β-unsaturated esters. These salts may be formed from any of the strong acids including hydrochloric, nitric, and sulfuric acids as well as the salts of the weaker acetic acid. The only criteria for such salts is that they must be salts of ammonia or of metals selected from the group consisting of lithium, zinc, cadmium, cerium and lead, and the salts must be sufficiently soluble in the organic solvent used in conducting the process so as to catalyze the reaction in accordance with the present invention.

As indicated in the reaction sequence noted earlier, the alkyl acetoacetic ester and ammonia react in equimolar proportions. The method of this invention can, therefore, be carried out by employing approximately equimolar ratios of these reactants in the presence of the selected catalysts. Variations in the proportion of reactants can be used, however, without significant differences in the results. It has been found that a considerably more rapid reaction rate can be obtained by employing a substantial excess of ammonia. In the preferred embodiment of this process, as much as 2 moles of ammonia or more per mole of alkyl acetoacetic ester are employed and thus is obtained a rapid reaction rate and high yield in a short period of time.

Ammonia gas may also be used as such in accordance with the present invention. It is sufficient that such gas be passed into a stirred reaction mixture of ester, catalyst and water-containing solvent until the solution is neutralized. By neutralized is meant until the enol form of acetoacetic ester is completely reacted as determined by a neutral reaction medium. For example, when the pH of the reaction medium becomes slightly basic, e.g., pH 7.0, the acetoacetic ester is completely reacted.

The amount of organic solvent, i.e., ethanol or methanol, must be sufficient to provide an adequately fluid reaction mixture and dissolve the aforementioned catalytic salt sufficiently to obtain the desired catalytic effect. For instance, an amount of solvent about double the volume of alkyl acetoacetic ester can be used. With a lesser amount of solvent, the mixture is too concentrated and the metal salts do not easily pass sufficiently into solution. Preferably, the amount of solvent is several times the amount of ester used, for example 2 to 10 times greater than the volume of such ester. When ammonia gas is used as the reactant, sufficient water must be added to the reaction system so as to readily dissolve the gas at reaction conditions. It has been found convenient to add water up to 50% of the volume of organic solvent in such embodiment.

The amount of ammonium salt or metal salt catalyst used in the reaction mixture must only be sufficient to cause the two reactants to react at room temperature sufficiently rapidly so as to achieve an economical rate of reaction. As little as 0.01 mole of catalyst per mole of alkyl acetoacetate ester can be used to achieve such reaction. However, amounts of catalytic salts as high as 1.5 mole per mole of acetoacetic ester can also be used. The preferred amount of salts is from 0.30 to 1.00 mole per mole of alkyl acetoacetic ester, with a 0.5:1.0 ratio of catalyst:ester being most preferred.

The initial reaction mixture comprising the catalytic salt, ammonia (when in aqueous solution), and the alkyl acetoacetic ester is stirred at room temperature without any necessity for temperature control, e.g., the reaction is not highly exothermic. Usually no more than 16 hours is necessary to complete the reaction at this temperature. Reaction times as little as 1 hour at room temperature are sufficient to generate recoverable amounts of product. While it is possible to conduct the reaction at temperatures higher than ambient, for example, up to the reflux temperature of the organic solvent system, thereby giving even shorter reaction times, such shorter times are achieved at the expense of an increase in undesirable by-products and a concurrent decrease in the desired $\beta$-amino ester. Temperatures up to 80° C. are useful in conducting the process in accordance with this invention. However, preferred reaction times are from 7 to 16 hours preferably at room temperature (25° C.). After this period, the reaction mass is extracted with a solvent that dissolves the $\beta$-amino $\alpha,\beta$-unsaturated ester formed during the reaction. Solvents such as the low molecular weight alkanes have proven to be effective for use in the process in accordance with the present invention. Particularly preferred as such solvent is hexane.

The product resulting from the above extraction is of sufficient purity so that no further treatment such as distillation is required. This greatly simplifies the preparative and extractive procedures.

The following examples illustrate preparation of certain $\beta$-amino derivatives of $\alpha,\beta$-unsaturated esters by specific embodiments of the method of this invention.

The following preparative procedure has been found useful for the synthesis of alkyl acetoacetate esters. This general preparation is exemplified by the preparation of 2-ethylhexyl acetoacetate.

EXAMPLE 1

Diketene, 210 gm (1.76 mole) was added to 390 gm (2.07 mole) of 2-ethylhexanol and 1.1 gm p-toluene sulfonic acid at 94°-107° C. The reaction mass was held at around 105° C. for 1.5 hours. After this period of time had elapsed, the reaction product was washed with water, dried with anhydrous magnesium sulfate and distilled. 2-ethylhexyl acetoacetate was collected in the fraction boiling 96°-101° C., 1 mm Hg. The product was obtained in 87% yield.

The catalyzed amination reactions are illustrated in the following examples.

EXAMPLE 2

Zinc acetate dihydrate, 66 gm (0.3 mole), was mixed with 300 cc of ethanol and 78 gm (0.6 mole) of ethyl acetoacetate was added thereto. The solution formed from this first step was neutralized with 124 gm (2 mole) of concentrated ammonium hydroxide. After standing overnight, the precipitate was filtered out and the filtrate was extracted with hexane. The extractant was evaporated to remove hexane and the residue fractionally distilled to give the fraction boiling 98°-98° C./1 mm of mercury, ethyl, 3-amino crotonate, 101 gm (94%).

EXAMPLE 3

Lithium acetate dihydrate, 10.2 gm (0.1 mole) was dissolved in 100 cc of a 90% aqueous solution of methanol and 43 gm (0.2 mole) of 2-ethylhexyl acetoacetate was added thereto. The resulting solution was neutralized with 12.4 gm (0.20 mole) concentrated ammonium hydroxide. After standing overnight at room temperature, the resulting reaction solution was extracted with hexane, dried with magnesium sulfate and the hexane extractant was evaporated. A yield of 21.0 gm of 2-ethylhexyl 3-amino crotonate was obtained (90%).

The table below illustrates the effectiveness of catalysts in accordance with the present invention. In all cases disclosed, 2-ethylhexyl acetoacetate:ammonium hydroxide was used in 1:2, the reaction carried out at 25° C. and then allowed to stand overnight, e.g., 16 hours before determining the product yields. This is the procedure identical to that disclosed in Example 2. Catalyst moles is based on moles of ester employed, e.g., 1.0 moles of catalyst is 1:1 ester:catalyst and 0.01 moles of catalyst is 1:0.01 ester:catalyst.

| Example | Catalyst Composition | Catalyst Moles | Yield of alkyl 3-amino crotonate |
|---|---|---|---|
| 3 | Lithium acetate | 1.0 | 89 |
| 4 | Lithium acetate | 0.5 | 90 |
| 5 | Lithium acetate | 0.3 | 84 |
| 6 | Lithium acetate | 0.1 | 76 |
| 7 | Lithium acetate | 0.01 | 69 |
| Comparative | | — | 68 |
| 8 | Zinc acetate | 0.5 | 91 |
| 9 | Lead acetate | 0.5 | 100 |
| 10 | Cadmium acetate | 0.5 | 95 |
| 11 | Ammonium acetate | 1.0 | 91 |

EXAMPLE 12

Lithium acetate dihydrate, 5.1 g (.05 mole), was dissolved in 100 ml methanol and 17.4 g (0.10 mole) 2-ethoxyethyl acetoacetate added. Conc. NH$_4$OH 12.4 g (.2 mole) were added. After standing 16 hours at 25° C. gc showed 70% conversion of 2-ethoxyethyl acetoacetate to 2-ethoxyethyl 3-amino crotonate. Product was extracted with hexane and then with methylene chloride. Total yield was 17.0 g, 73%.

EXAMPLE 13

Lithium acetate dihydrate, 5.1 g (.05 mole), was dissolved in 100 ml methanol, 20.2 g (0.1 mole) 2-butoxyethyl acetoacetate were added followed by adding 12.4 g (0.2 mole) conc. $NH_4OH$. After standing 16 hours at 25° C., the gc showed 79% conversion of the 2-butoxyethyl acetoacetate to 2-butoxyethyl 3-amino crotonate. 2-butoxyethyl 3-amino crotonate product was extracted with hexane and with methylene chloride. Total yield was 17.4 g, 76%.

EXAMPLE 14

Example 13 was repeated in its entirety, but samples were taken at approximately 30 minutes, 1 hour, 4 hours, 6 hours and 7 hours. Analysis by gas chromotography (gc) gave yields of 20%, 38%, 42%, 55% and 62%, respectively. An identical experiment, but without the presence of any catalyst, gave the following yields: 2%, 10%, 19%, 25% and 22%, respectively.

EXAMPLE 15

Example 14 was repeated in its entirety, but the reaction temperature was raised from 25° C. to 55° C. Samples were taken at 15 minutes, 1 hour, 3 hours, 4 hours, and 6 hours. Analysis of the reaction mass gave the following yields of 2-butoxyethyl-3-amino crotonate: 42%, 63%, 70%, 67%, and 60%, respectively.

What is claimed is:

1. A method for preparing $\beta$-amino derivatives of $\alpha,\beta$-unsaturated esters of the formula $CH_3C(NH_2)=CHC(O)OR'$ wherein R' is $C_1$ to $C_{10}$ linear or branched alkyl or substituted $C_1$ to $C_{10}$ linear or branched alkyl, the substituents being those that would not interfere with the reaction, which comprises:
   a. forming a reaction mixture of an alkyl acetoacetate ester of the formula $CH_3C(O)CH_2C(O)OR'$ wherein R' is the same as defined above,
      1. with ammonia and
      2. a salt of a metal selected from the group consisting of lithium, zinc, cadmium, cerium, lead or mixtures thereof in an organic solvent; said salt being soluble in said organic solvent in an amount sufficient to catalyze the reaction between said ester and said ammonia; and
   b. recovering said $\beta$-amino derivative of $\alpha,\beta$-unsaturated ester.

2. The method of claim 1 wherein the ammonia is concentrated ammonium hydroxide.

3. The method of claim 1 wherein R' is selected from the group consisting of $C_1$ to $C_8$ linear or branched alkyl and $C_1$ to $C_4$ alkoxy substituted $C_1$ to $C_8$ linear or branched alkyl.

4. The method of claim 1 wherein 0.05 to 1.50 mole of said salt per mole of said alkyl acetoacetate ester is added to said reaction mixture.

5. The method of claim 1 wherein salt is selected from the group consisting of lead acetate, lithium acetate, or mixtures thereof.

6. The method of claim 1 wherein the said catalyzed reaction is carried out at 25°–80° C. from 1 to 16 hours.

7. The method of claim 6 wherein said catalyzed reaction is carried out at 25° C. from 7 to 16 hours.

* * * * *